US005616774A

United States Patent [19]
Evans et al.

[11] Patent Number: 5,616,774
[45] Date of Patent: Apr. 1, 1997

[54] INHIBITION OF UNSATURATED MONOMERS WITH 7-ARYL QUINONE METHIDES

[75] Inventors: Samuel Evans, Marly, Switzerland; Matthew E. Gande, New Fairfield, Conn.; Peter Nesvadba, Yorktown Heights, N.Y.; Volker H. von Ahn, Mahopac, N.Y.; Roland A. E. Winter, Armonk, N.Y.

[73] Assignee: Ciba-Geigy Corporation, Tarrytown, N.Y.

[21] Appl. No.: 422,284

[22] Filed: Apr. 14, 1995

[51] Int. Cl.$^6$ .................................................. C07C 69/00
[52] U.S. Cl. ........................ 560/4; 585/3; 585/4; 585/5
[58] Field of Search ................... 560/205, 4; 585/3, 585/4, 5

[56] References Cited

U.S. PATENT DOCUMENTS

| | | | |
|---|---|---|---|
| 4,003,800 | 1/1977 | Bacha et al. | 203/9 |
| 4,032,547 | 6/1977 | Bacha et al. | 260/396 |
| 4,040,911 | 8/1977 | Bacha et l. | 203/9 |
| 5,221,764 | 6/1993 | Roling | 560/205 |
| 5,254,760 | 10/1993 | Winter et al. | 585/5 |

FOREIGN PATENT DOCUMENTS 0522709  1/1993  European Pat. Off. .

OTHER PUBLICATIONS

Chemical Abstracts 70:38158, Brindley et al Date 1968.
Chem. Abstr. 108:38591, Mukoyama et al Date 1987.
Chem. Abstr. 90: 186075q, 1979.
Chem. Abst. 10th Cell. Index p. 5199CS, 1979.
S. Agric. Food Chem. vol. 27, No. 5 1979 pp. 1007–1016.
Methoden Der Organis Chem Chemie (Houben–Weyl) Band VII/3b 1979 E. Miller et al pp. 420–427.

Primary Examiner—Samuel Barts
Attorney, Agent, or Firm—Luther A. R. Hall

[57] ABSTRACT

Ethylenically unsaturated monomers are protected from premature polymerization during manufacture and storage by the incorporation therein of an effective stabilizing amount of a 7-aryl quinone methide compound.

26 Claims, No Drawings

INHIBITION OF UNSATURATED MONOMERS WITH 7-ARYL QUINONE METHIDES

The present invention relates to a compositions and a process for reducing premature polymerization of readily polymerizable unsaturated monomers during monomer manufacturing processes by incorporating therein an effective amount of a 7-aryl quinone methide compound.

BACKGROUND OF THE INVENTION

It is well known that ethylenically unsaturated monomers like vinyl aromatic compounds, such as styrene, α-methylstyrene, vinyltoluene or divinylbenzene or acrylic monomers, such as acrylic acid, methacrylic acid and their esters and amides, or unsaturated esters such as vinyl acetate or unsaturated polyesters have a strong tendency to polymerize when subjected to elevated temperatures. Manufacturing processes for such monomers typically include distillations or handling at elevated temperatures.

To prevent the premature polymerization of vinyl aromatic monomers during the distillation purification process, various compounds have been disclosed as polymerization inhibitors. These include elemental sulfur and many classes of organic chemicals having varying degrees of success in industrial use. These compounds include among others nitrated phenol derivatives, C- and N-nitroso compounds, nitroxyl derivatives, diphenylamines, hydroxylamines, quinones, quinone oximes and quinone alkide derivatives.

Known inhibitors of acrylic monomer polymerization include phenothiazine, hydroquinone monomethyl ether, and methylene blue. Phenothiazine, while unable to totally inhibit polymerization of acrylic monomers, is a commonly used co-additive. Recent patents claim phenylenediamines with soluble transition metal salts(U.S. Pat. No. 5,221,764) and aryl N-nitroso compounds(EP 0 522 709 A2) are active in acrylic monomer stabilization. However, them still remains a need for a compound to improve the stability of acrylic monomers during their distillation. The need exists for a stable polymerization inhibitor system which will effectively and safely prevent the premature polymerization of unsaturated monomers during distillation and purification processes, particularly if air is absent.

U.S. Pat. Nos. 4,003,800 and 4,040,911 disclose the use of quinone alkides in a styrene purification process. U.S. Pat. No. 4,032,547 describes the preparation of quinone methides from phenols by a persulfate oxidation process mediated by ferricyanide.

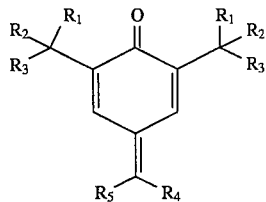

In the generic structure depicted above, groups $R_4$ and $R_5$ include phenyl and substituted phenyl, but such structures are not exemplified in U.S. Pat. No. 4,003,800 nor is any 7-aryl quinone methide derivative included among the 17 individually named compounds in U.S. Pat. No. 4,003,800. All 17 compounds have either no substituents or an alkyl substituent in the 7-position. The individually named compounds in U.S. Pat. No. 4,003,800 include six with unsubstituted 7-methylene groups, which are clearly too thermally unstable for practical use as industrial polymerization inhibitors in unsaturated monomers.

There is much convincing experimental evidence proving that quinone methides unsubstituted in the 7-position, i.e. compounds with an unsubstituted exomethylene group, are in fact too unstable to be even isolated at room temperature. These methylene derivatives can be prepared only as a very dilute 10-3 to 10-5 molar solutions which are stable only few days in the absence of light (See, e.g.,: P. Gruenanger in Houben-Weyl, Methoden der Organischen Chemie, Vol. 7/3B, p. 420).

Quinone methides with 7-alkyl groups also lack thermal stability to be used efficiently in the present application.

Surprisingly, quinone methides with 7-aryl substituents have now been found to be much more thermally stable than 7-alkyl derivatives. For example, the 2,6-di-tert-butyl-4-isobutylidene quinone methide B decomposed into material inactive as an inhibitor of styrene polymerization on prolonged storage at room temperature whereas 7-phenyl quinone methide C is completely stable. Another convincing piece of evidence for the inherent instability of 7-alkyl quinone methides is obtained by Differential Scanning Calorimetry (DSC), see Table 1 below. The 7-alkyl quinone methides A and B exhibited strong exothermy in J/g associated with their decomposition when heated under nitrogen, whereas the 7-phenyl quinone methide C showed no exothermy at all.

TABLE 1

| Quinone methide | A | B | C |
|---|---|---|---|
| Exothermy in DSC under nitrogen | 130 J/g | 175 J/g | 0 |

OBJECTS OF THE INVENTION

One object of this invention is to provide a composition protected from premature polymerization and a process for inhibiting the premature polymerization of ethylenically unsaturated monomers during the distillation and purification steps by incorporating therein an effective amount of at least one 7-aryl quinone methide derivative alone or in combination with another inhibitor.

A further object of this invention is to provide new and novel 7-aryl quinone methide compounds suitable as stabilizers for the instant process and compositions.

DETAILED DESCRIPTION

The instant invention pertains to a composition for inhibiting the premature polymerization of an ethylenically unsaturated monomer which comprises (a) an ethylenically unsaturated monomer or mixture of monomers, and (b) an effective inhibiting amount of a compound of formula I

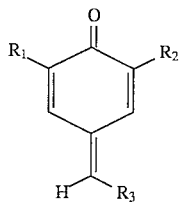

where

R₁ and R₂ are independently alkyl of 4 to 18 carbon atoms, cycloalkyl of 5 to 12 carbon atoms or phenylalkyl of 7 to 15 carbon atoms, and R₃ is 2-, 3- or 4-pyridyl, 2- or 3-thienyl, 2- or 3-pyrryl, 2- or 3-furyl, aryl of 6 to 10 carbon atoms, or said aryl substituted by one to three alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms, alkoxycarbonyl of 2 to 8 carbon atoms, hydroxy, nitro, amino, cyano, carboxy, aminocarbonyl, chloro or mixtures of said substituents.

Preferably, in the compound of formula I, $R_1$ and $R_2$ are the same. Preferably, $R_1$ and $R_2$ are tert-butyl, tert-amyl, tert-octyl, cycloalkyl, α-methylbenzyl or α,α-dimethyl-benzyl; most preferably $R_1$ and $R_2$ are tert-butyl, tert-amyl or tert-octyl.

Preferably, in the compound of formula I, $R_3$ is phenyl or phenyl substituted by nitro, cyano, dimethylamino, methoxy, alkyl of 1 to 4 carbon atoms, hydroxy or mixtures of said substituents; most preferably $R_3$ is phenyl.

The monomer of the instant invention is an aromatic vinyl compound or an acrylic monomer.

The effective inhibiting amount of a compound of formula I is from 1 to 2000 ppm, based on the weight of the monomer.

Some preferred compounds of formula I are
2,6-di-tert-butyl-4-benzylidene-cyclohexa-2,5-dienone,
2,6-di-tert-butyl-4-(4-nitrobenzylidene)-cyclohexa-2,5-dienone,
2,6-di-tert-butyl-4-(3-nitrobenzylidene)-cyclohexa-2,5-dienone,
2,6-di-tert-butyl-4-(4-cyanobenzylidene)-cyclohexa-2,5-dienone,
2,6-di-tert-butyl-4-(4-dimethylaminobenzylidene)-cyclohexa- 2,5-dienone,
2,6-di-tert-amyl-4-benzylidene-cyclohexa-2,5-dienone,
2,6-di-tert-butyl-4-(4-methoxybenzylidene)-cyclohexa-2,5-dienone, and
2,6-di-tert-butyl-4-(3,5-di-tert-butyl4-hydroxybenzylidene)-cyclohexa- 2,5-dienone; especially 2,6-di-tert-butyl-4-benzylidene-cyclohexa-2,5-dienone.

It is emphasized that the instant compounds of formula I differ significantly from the structurally related compounds of U.S. Pat. No. 4,003,800 in that the instant compounds are thermally stable and the compounds of U.S. Pat. No. 4,003,800 are not. The thermal stability of the instant compounds allows them to be used practically as polymerization inhibitors unlike the compounds of the prior art.

The instant invention also pertains to a process for inhibiting the premature polymerization of an ethylenically unsaturated monomer which comprises adding thereto an effective inhibiting amount of a compound of formula I.

The instant invention especially pertains to a composition for inhibiting the premature polymerization of an ethylenically unsaturated monomer which comprises (a) an ethylenically unsaturated monomer or mixture of monomers, and (b) an effective inhibiting amount of a synergistic mixture of (i) at least one compound of formula I

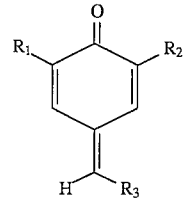

where

R₁ and R₂ are independently alkyl of 4 to 18 carbon atoms, cycloalkyl of 5 to 12 carbon atoms or phenylalkyl of 7 to 15 carbon atoms, and R₃ is 2-, 3- or 4-pyridyl, 2- or 3-thienyl, 2- or 3-pyrryl, 2- or 3-furyl, aryl of 6 to 10 carbon atoms, or said aryl substituted by one to three alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms, alkoxycarbonyl of 2 to 8 carbon atoms, hydroxy, nitro, amino, cyano, carboxy, aminocarbonyl, chloro or mixtures of said substituents, and (ii) at least stable one nitroxyl compound.

The relative concentrations of component (i) is 5 to 95 percent by weight and of component (ii) is 95 to 5 percent by weight based on the combined total weight of components (i) and (ii) and wherein the effective inhibiting amount of the synergistic mixture of components (i) and (ii) is 1 to 2000 ppm based on the total weight of the monomer of component (a).

The instant invention also pertains to a process of inhibiting premature polymerization of an ethylenically unsaturated monomer which comprises adding effective inhibiting amount of the synergistic mixture described above.

The monomers in the instant process are processed at a temperature from 50° C. to 150° C.

The synergistic mixture of the instant invention is added continuously or added intermittently upstream to the points where polymerization inhibition is required. In another variation of the instant invention, the components (i) and (ii) of the synergistic mixture are added separately at different entry points into the process stream in the processing train.

Some preferred embodiments of component (i) are
2,6-di-tert-butyl-4-benzylidene-cyclohexa-2,5-dienone,
2,6-di-tert-butyl-4-(4-nitrobenzylidene)-cyclohexa-2,5-dienone,
2,6-di-tert-butyl-4-(3-nitrobenzylidene)-cyclohexa-2,5-dienone,
2,6-di-tert-butyl-4-(4-cyanobenzylidene)-cyclohexa-2,5-dienone,
2,6-di-tert-butyl-4-(4-dimethylaminobenzylidene)-cyclohexa-2,5-dienone,
2,6-di-ten-amyl-4-benzylidene-cyclohexa-2,5-dienone,
2,6-di-tert-butyl-4-(4-methoxybenzylidene)-cyclohexa-2,5-dienone, and
2,6-di-tert-butyl-4-(3,5-di-tert-butyl-4hydroxybenzylidene)-cyclohexa-2,5-dienone.

Some preferred embodiments of component (ii) are
1-oxyl-2,2,6,6-tetramethylpiperidine,
1-oxyl-2,2,6,6-tetramethylpiperidin-4-ol,
1-oxyl-2,2,6,6-tetramethylpiperidin-4-one, 1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl)adipamide,
N-1-oxyl-2,2,6,6-tetramethylpiperidin-4-yl-caprolactam,
N-1-oxyl-2,2,6,6-tetramethylpiperidin-4-yl-dodecylsuccinimide,
2,4,6-tris-[N-butyl-N-(1-oxyl-2,2,6,6-tetramethylpiperidin-4 -yl]-s-triazine,
4,4'-ethylenebis(1-oxyl-2,2,6,6-tetramethylpiperazin-3-one) and
di-tert-butyl nitroxyl.

A most preferred embodiment of the instant invention is where component (i) is 2,6-di-tert-butyl-4-benzylidene-cyclohexa-2,5-dienone, and component (ii) is bis (1-oxyl-2,2,6,6-tetramethylpiperidin-4-yl) sebacate.

The term unsaturated monomers as used in this application includes any readily polymerizable vinyl aromatic monomer, e.g., styrene, α-methylstyrene, vinyltoluene, divinylbenzene and structural isomers, derivatives and mixtures thereof or acrylic monomer, such as acrylic acid, methacrylic acid or their esters and amides and mixtures thereof or unsaturated esters such as vinyl acetate and unsaturated polyesters and mixtures thereof.

The effective mount of the hindered 7-aryl quinone methide polymerization inhibitor may vary over a wide range depending upon the particular ethylenically unsaturated monomer and the conditions of distillation and/or storage. Preferably, the effective inhibiting total amount of a quinone methide is from 1 ppm to about 2000 ppm (based upon the weight of the monomer being inhibited). For most applications the inhibitor system is used in the range of 5 to 1000 ppm. As the temperature increases, greater amounts of inhibitor are required.

It has also been found that the hindered 7-aryl quinone methides show strong synergistic effect when used with stable hindered nitroxyl free radicals. Surprisingly effective inhibition of ethylenically unsaturated monomer polymerization is thus obtained using combinations of hindered 7-aryl quinone methides with a wide variety of free nitroxyl radical derivatives, for example compounds such as:
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis( 1-oxyl-2,2,6,6-tetramethylpiperidin-4-yl)adipamide,
N-1-oxyl-2,2,6,6-tetramethylpiperidin-4-yl-caprolactam,
N-1-oxyl-2,2,6,6-tetramethylpiperidin-4-yl-dodecylsuccinimide,
2,4,6-tris-[N-butyl-N-(1-oxyl-2,2,6,6-tetramethylpiperidin-4 -yl]-s-triazine,
4,4'-ethylenebis(1-oxyl-2,2,6,6-tetramethylpiperazin-3-one) and
di-tert-butyl nitroxyl.

The relative concentrations of nitroxyl radical and hindered 7-aryl quinone methide compound used in the instant invention are generally in the range of about 5 to 95 weight percent nitroxyl radical and 95 to 5 weight percent hindered 7-aryl quinone methide, based on the total combined weight of these components. In preferred embodiments, the concentrations generally fall in the range of about 10 to 90 weight percent nitroxyl radical and 90 to 10 weight percent hindered 7-aryl quinone methide based on the total combined weight of these components.

The polymerization inhibitor compositions can be introduced into the monomer to be protected by any conventional method. It may be added as a concentrate solution in suitable solvents just upstream of the point of desired application by any suitable means. In addition, these compounds may be injected separately into the distillation train along with the incoming feed, or through separate entry points providing efficient distribution of the inhibitor composition. Since the inhibitor is gradually depleted during operation, it is generally necessary to maintain the appropiate amount of the inhibitor in the distillation apparatus by adding inhibitor during the course of the distillation process. Such addition may be carried out either on a generally continuous basis or it may consist of intermittently charging inhibitor into the distillation system if the concentration of inhibitor is to be maintained above the minimum required level.

The polymerization inhibiting compositions of this invention are also well suited for protecting the reboiler sections of a distillation column.

The following examples are meant for illustrative purposes only and are not to be construed as limiting the instant invention in any manner whatsoever.

In the Examples, styrene is used as a representative vinyl aromatic monomer and the mixture acrylic acid-octyl acrylate serves as a test monomer for acrylate monomers.

EXAMPLE 1

2,6-Di-tert-butyl-4-benzylidene-cyclohexa-2,5-dienone

This compound is prepared according to the method described by B. Koutek et al., Synth. Commun. 6 (4), 305 (1976).

EXAMPLE 2

2,6-Di-tert-butyl-4-(4-nitrobenzylidene)-cyclohexa-2,5-dienone (A) 2,6-Di-tert-butyl-4-[4-nitro-α-(piperidin-1-yl)benzyl]phenol A mixture of 2.1 g (0.01 mol) of 2,6-di-tert-butylphenol, 1.51 g (0.01 mol) of 4-nitrobenzaldehyde and 0.9 g (0.0105 mol) of piperidine is refluxed under nitrogen in 15 ml n-butanol for 24 hours. The solution is then evaporated in vacuo. The residue is then chromatographed on silica gel with hexane:ethyl acetate (4:1 ). The pure fractions are recrystallized from acetonitrile to give 1.0 g of the title compound as pale yellow crystals, melting at 147°–148° C.

$^1$H-NMR(CDCl$_3$, 500 MHz): 1.25 s (2x t-Bu), 1.30–1.60 m (3x CH$_2$), 2.10–2.25 m (2x CH$_2$), 4.20 s (CH), 5.05 s (OH), 7.03 s (2 ArH), 7.52 d(2 ArH, J=8.3 Hz), 8.06 d (2 ArH, J=8.3 Hz).

(B) 2,6-Di-tert-butyl-4-(4-nitrobenzylidene)-cyclohexa-2,5-dienone

A mixture of 4.24 g (0.01 mol) of the compound made in Example 2(A) and 3.0 g (0.024 mol) of dimethyl sulfate is refluxed in 15 ml acetonitrile for one hour. An additional 0.8 g (0.006 mol) of dim ethyl sulfate is added and refluxing is continued for another hour. The solution is then evaporated in vacuo and the residue chromatographed on silica gel with toluene. The pure fractions are recrystallized from acetonitrile to give 2.7 g of the title compound as orange crystals, melting at 162°–163° C.

$^1$H-NMR(CDCl$_3$, 300 MHz): 1.26 s (t-Bu), 1.30 s (t-Bu), 6.98 d (1 ArH, J=2.8 Hz), 7.11 s (CH), 7.33 d (1 ArH, J=2.8 Hz), 7.55 d (2 ArH, J=8.4 Hz), 8.28 d (2 ArH, J=8.4 Hz).

EXAMPLE 3

2,6-Di-tert-butyl-4-(3-nitrobenzylidene)-cyclohexa-2,5-dienone (A) 2,6-Di-tert-butyl-4-[3-nitro-α-(piperidin-1-yl)benzyl] phenol Using the same procedure described in Example 4, 30.2 g (0.2 mol) of 3-nitro-benzaldehyde, 37.4 g (0.44 mol) of piperidine and 39.2 g (0.19 mol) of 2,6-di-tert-butyl-phenol are allowed to react in xylene to give 48.4 g of the title compound as yellow crystals, melting at 157° C.

| Analysis: | |
|---|---|
| Calcd for C$_{26}$H$_{36}$N$_2$O$_3$: | C, 73.55; H, 8.55; N, 6.60. |
| Found: | C, 73.65; H, 8.53; N, 6.65. |

(B) 2,6-Di-tert-butyl-4-(3-nitrobenzylidene)-cyclohexa-2,5-dienone

The compound prepared in Example 3(A), 17.0 g (0.04 mol) is heated in 60 ml acetic anhydride at 80° C. for 45 minutes. The mixture is then poured into 150 ml water and extracted with toluene. The toluene layer is washed three times with water, evaporated in vacuo, and recrystallized from methanol to give 9.7 g of the title compound as an orange solid, melting at 118° C.

| Analysis: | |
|---|---|
| Calcd for C$_{21}$H$_{25}$NO$_3$: | C, 74.3; H, 7.4; N, 4.1. |
| Found: | C, 74.1; H, 7.4; N, 4.1. |

EXAMPLE 4

2,6-Di-tert-butyl-4-(4-cyanobenzylidene)-cyclohexa-2,5-dienone (A) 2,6-Di-tert-butyl-4-[4-cyano-α-(piperidin-1-yl )benzyl]phenol 2,6-Di-tert-butylphenol (4.12 g, 0.02 mol), 2.62 g (0.02 mol) of 4-cyano-benzaldehyde and 1.7 g (0.02 mol) of piperidine are refluxed under nitrogen in 25 ml of xylene for 24 hours. The solution is then evaporated in vacuo and the residue chromatographed on silica gel with toluene/ethyl acetate (9:1) to give 6.2 g of a practically pure title compound. A 5 g portion of said compound is recrystallized twice from acetonitrile to give 1.0 g of a pure sample as colorless crystals, melting at 139°–140° C.

$^1$H-NMR(CDCl$_3$, 300 MHz): 1.36 s (2x t-Bu), 1.35–1.60 g (3x CH$_2$), 2.10–2.30 g (2x CH$_2$), 4.15 s (CH), 5.05 s (OH), 7.04 s (2 ArH), 7.46–7.55 g (4 ArH).

(B) 2,6-Di-tert-butyl-4-(4-cyanobenzylidene)-cyclohexa-2,5-dienone

The compound of Example 4(A) (1.2 g, 0.003 mol) and 1.1 g (0.009 mol) of dimethyl sulfate are refluxed in 20 ml of acetonitrile for one hour. The solution is then evaporated in vacuo and the residue chromatographed on silica gel with toluene. The pure fractions are recrystallized from acetonitrile to give 0.3 g of the title compound as yellow crystals, melting at 147°–148° C.

$^1$H-NMR(CDCl,300 MHz): 1.25 s (t-Bu), 1.29 s (t-Bu), 6.96 d (1 ArH, J=2.2 Hz), 7.08 s (CH), 7.32 d (1 ArH, J=2.2 Hz), 7.50 d (2 ArH, J=8.3 Hz), 7.70 d (2 ArH, J=8.3 Hz).

EXAMPLE 5

2,6-Di-tert-butyl-4-(4-dimethylaminobenzylidene)-cyclohexa-2,5-dienone (A) 2,6-Di-tert-butyl-4-[4-dimethylamino-α-(piperidin-1-yl)benzyl]phenol To 30.4 g (0.2 mol) of 4-dimethylaminobenzaldehyde in 100 ml of xylene, 39.1 g (0.46 mol) of piperidine is added dropwise over a period of six minutes. The mixture is heated at reflux using a Dean-Stark trap until the separation of water is complete. To the cooled reaction mixture 40.3 (0.2 mol) of 2,6-di-tert-butylphenol in 70 ml of xylene is added rapidly. The mixture is then heated at reflux for five hours. The title compound is isolated as an almost white solid by evaporation of the solvent and recrystallization from toluene-hexane. The yield is 66.3 g of the title compound, melting at 184°–185° C.

| Analysis: | |
|---|---|
| Calcd for C$_{28}$H$_{42}$N$_2$O: | C, 79.6; H, 10.0; N, 6.6. |
| Found: | C, 79.7; H, 10.1; N, 6.4. |

(B) 2,6-Di-tert-butyl-4-(4-dimethylaminobenzylidene)-cyclohexa-2,5-dienone

The compound prepared in Example 5(A) (21.1 g. 0.05 mol) is heated in 100 ml acetic acid at 110° C. for 15 minutes. The reaction mixture is poured into 200 ml of water and then taken up in 200 ml of toluene. Evaporation of the solvent and recrystallization of the residue from methanol affords 10.7 g of the title compound as a red powder, melting at 175° C.

| Analysis: | |
|---|---|
| Calcd for C$_{23}$H$_{31}$NO: | C, 81.8; H, 9.3; N, 4.1. |
| Found: | C, 81.7; H, 9.2; N, 4.1. |

EXAMPLE 6

2,6-Di-tert-amyl-4-benzylidene-cyclohexa-2,5-dienone 6.0 g (0.026 Mol) of 2,6-di-tert-amylphenol, 2.75 g (0.026 mol) of benzaldehyde and 4.37 g (0.05 1 mol) of piperidine are refluxed under nitrogen in 50 ml of heptane on a Dean-Stark trap for 24 hours. The solution is then evaporated in vacuo and the residue chromatographed twice on silica gel with hexane and then with hexane:ethyl acetate (9:1) to give 3.5 g of the title compound as a thick yellow oil.

$^1$H-NMR(CDCl,300 MHz): 0.66 t (CH$_3$, J=7.3 Hz), 0.68 t (CH$_3$, J=7.3 Hz), 1.24 s (CH$_3$), 1.28 s (CH$_3$), 1.83 q(CH2, J=7.3 Hz), 1.87 q(CH$_2$, J=7.3 Hz), 6.98 d (1 ArH, J=2.1 Hz), 7.19 s (CH), 7.36–7.45 g (1 ArH), 7.45–7.52 g (5 ArH).

EXAMPLE 7

2,6-Di-tert-butyl-4-(4-methoxybenzylidene)-cyclohexa-2,5-dienone

This compound is prepared according to the method described by L. Jurd et al., J. Agric. Food Chem., 27, 1007 (1979).

EXAMPLE 8

2,6-Di-tert-butyl-4-(3,5-di-tert-butyl-4-hydroxybenzylidene)-cyclohexa-2,5-dienone This compound is prepared according to the method described by A. G. Liakumovich et al., Izobreteniya, 37, 87 (1992).

EXAMPLE 9

Inhibition of Styrene Monomer (A) Series of 7-aryl quinone methides

Commercial grade styrene is freed of tert-butyl catechol storage stabilizer by washing with 1N sodium hydroxide, water and subsequent distillation under reduced pressure. A 300 mL 3-necked flask equipped with thermometer, condenser, rubber septum and magnetic stirrer bar is charged with 100 g of purified styrene and 20.0 mg of experimental inhibitor or 20 mg of a mixture of inhibitors, yielding styrene with 200 ppm of total inhibitors. An oxygen-free atmosphere is established by five consecutive evacuations and backfilling with nitrogen, followed by sparging the styrene solution with pure nitrogen for 15 minutes. The vessel is then immersed into a mechanically stirred and thermostatically controlled oilbath at 120° C. and heated for 45 minutes. The amount of polystyrene formed is then determined by refractive index measurements, calibrated with authentic polystyrene in styrene solutions of known concentration. Without any added inhibitor 6.2% polystyrene is formed. Polymer levels obtained with inhibitors are listed in the table below.

| Compound of Example | Percent Polymer after 45 Minutes |
|---|---|
| 1 | 0.48 |
| 2 | 0.32 |
| 3 | 0.32 |
| 4 | 0.32 |
| 5 | 1.13 |
| 6 | 0.48 |
| 7 | 0.65 |
| 8 | 0.48 |

Each of these 7-aryl quinone methides is quite effective as a polymerization inhibitor for styrene monomer.

(B) Concentration Dependence

The dependence of the amount of the styrene polymer formed on the concentration of the hindered 7-aryl quinone methide is illustrated in the table below. The 7-aryl quinone methide is the compound of Example 1.

| Concentration in ppm Compound of Example 1 | Percent Polymer after 45 Minutes |
|---|---|
| 100 | 0.97 |
| 200 | 0.48 |
| 500 | 0.00 |

It is clear that as the concentration of the inhibitor goes up the amount of polymer formed goes down. At 500 ppm the polymerization inhibition in this test is complete.

(C) Effect of Oxygen

When the compound of Example 1 is used in the presence of 0.66% oxygen or in the presence of only nitrogen, the amount of polymer formed after 45 minutes is the same, namely 0.48 %.

(D) Synergy with Stable Hindered Nitroxyl Free Radicals

The blends of hindered 7-aryl quinone methides with stable hindered nitroxyl free radicals inhibitors are found to be considerably more effective in reducing the amount of polymer formed than is either component by itself at the same total inhibitor concentration. This synergistic effect is demonstrated in the table below with the 7-aryl quinone methide compound of Example 1.

| Inhibitor | Concentration | Percent Polymer after 45 Minutes |
|---|---|---|
| Compound of Example 1 | 200 ppm | 0.48 |
| Nitroxyl* | 200 ppm | 1.37 |
| Compound of Example 1 + Nitroxyl* | 100 ppm + 100 ppm | 0.16 |

*Nitroxyl is bis(1-oxyl-2,2,6,6-tetramethylpiperidin-4-yl) sebacate.

It is clear that them is a synergistic effect obtained when a nitroxyl free radical is used in conjunction with the instant 7-aryl quinone methide.

EXAMPLE 10

Inhibition of Acrylate Monomers

A screening test that involves the radical polymerization of acrylate is developed to test polymerization inhibitors. The procedure involves the radical induced polymerization of a 3:1 mixture of acrylic acid and octyl acrylate in a low molecular weight carboxylic acid solvent. Free radicals are generated by the thermal decomposition of azo-bis-isobutyronitrile (AIBN) at 60° C. The degree of polymerization is determined by periodically measuring the solution viscosity, and comparing it to the initial viscosity. A four-fold increase in viscosity is considered failure.

Unless otherwise noted, all reagents and solvents are used as received. A solution of acrylate (3:1 weight ratio of acrylic acid to octyl acrylate) in propionic acid (0.1 g/mL) containing AIBN (recrystallized from methanol) and the inhibitor additive to be tested (2% and 400 ppm, respectively, with respect to acrylate) is prepared. When determining interaction with a coadditive, phenothiazine is present at 250 ppg (with respect to acrylate). To a Canon-Fenske viscometer is added 10 mL of the test solution, which is then purged with either nitrogen (>99.995%) or an oxygen gas mixture (6500 ppm oxygen in nitrogen) for 5 minutes before being heated in a 60° C. oil bath. After an additional purge for 5 minutes, drop times are automatically measured (10 minute intervals, with a 1 minute gas purge before each measurement) using a Design Scientific automated viscometer and a custom software package. The results are summarized in the table below.

|  | Time (min) to 4-Fold Viscosity Increase | |
| --- | --- | --- |
| Inhibitor (ppm) | Nitrogen | 6500 ppm Oxygen |
| None | 45 | 144 |
| Compound of Example 1 (400) | 69 | 147 |
| Phenothiazine (250) | 57 | 207 |
| Phenothiazine (250) plus Compound of Example 1 (400) | 73 | 221 |

The combination of an instant 7-aryl quinone methide plus phenothiazine provides superior polymerization inhibition compared to either inhibitor alone. The 7-aryl quinone methide inhibits the acrylate polymerization under nitrogen, but is ineffective under oxygen when used alone.

What is claimed is:

1. A composition for inhibiting the premature polymerization of an ethylenically unsaturated monomer which comprises
    (a) an ethylenically unsaturated monomer or mixture of monomers, and
    (b) an effective inhibiting amount of a compound of formula I

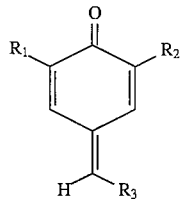

where
    $R_1$ and $R_2$ are independently alkyl of 4 to 18 carbon atoms, cycloalkyl of 5 to 12 carbon atoms or phenylalkyl of 7 to 15 carbon atoms, and
    $R_3$ is 2-, 3- or 4-pyridyl, 2- or 3-thienyl, 2- or 3-pyrryl, 2- or 3furyl, aryl of 6 to 10 carbon atoms, or said aryl substituted by one to three alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms, alkoxycarbonyl of 2 to 8 carbon atoms, hydroxy, nitro, amino, cyano, carboxy, aminocarbonyl, chloro or mixtures of said substituents.

2. A composition according to claim 1 where in the compound of formula I, $R_1$ and $R_2$ are the same.

3. A composition according to claim 2 wherein $R_1$ and $R_2$ are tert-butyl, tert-amyl, tert-octyl, cycloalkyl, α-methylbenzyl or α,α-dimethylbenzyl.

4. A composition according to claim 3 wherein $R_1$ and $R_2$ are tert-butyl, tert-amyl or tert-octyl.

5. A composition according to claim 1 where in the compound of formula I, $R_3$ is phenyl or phenyl substituted by nitro, cyano, dimethylamino, methoxy, alkyl of 1 to 4 carbon atoms, hydroxy or mixtures of said substituents.

6. A composition according to claim 5 where $R_3$ is phenyl.

7. A composition according to claim 1 wherein the monomer of component (a) is an aromatic vinyl compound or an acrylic monomer.

8. A composition according to claim 1 wherein the effective inhibiting amount of a compound of formula I is from 1 to 2000 ppm, based on the weight of the monomer of component (a).

9. A composition according to claim 1 wherein the compound of formula I is
2,6-di-tert-butyl-4-benzylidene-cyclohexa-2,5-dienone,
2,6-di-tert-butyl-4-(4-nitrobenzylidene)-cyclohexa-2,5-dienone,
2,6-di-tert-butyl-4-(3-nitrobenzylidene)-cyclohexa-2,5-dienone,
2,6-di-tert-butyl-4-(4-cyanobenzylidene)-cyclohexa-2,5-dienone,
2,6-di-tert-butyl-4-(4-dimethylaminobenzylidene)-cyclohexa-2,5-dienone,
2,6-di-tert-am yl-4-benzylidene-cyclohexa-2,5-dienone,
2,6-di-tert-butyl-4-(4-methoxybenzylidene)-cyclohexa-2,5-dienone, or
2,6-di-tert-butyl--4-(3,5-di-tert-butyl-4-hydroxybenzylidene)-cyclohexa-2,5-dienone.

10. A composition according to claim 1 where in the compound of formula I is 2,6-di-tert-butyl-4-benzylidene-cyclohexa-2,5-dienone.

11. A process for inhibiting the premature polymerization of an ethylenically unsaturated monomer which comprises
    adding thereto an effective inhibiting amount of a compound of formula I according to claim 1.

12. A composition for inhibiting the premature polymerization of an ethylenically unsaturated monomer which comprises
    (a) an ethylenically unsaturated monomer or mixture of monomers, and
    (b) an effective inhibiting amount of a synergistic mixture of
        (i) at least one compound of formula I

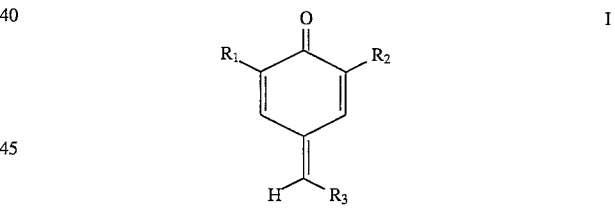

where
        $R_1$ and $R_2$ are independently alkyl of 4 to 18 carbon atoms, cycloalkyl of 5 to 12 carbon atoms or phenylalkyl of 7 to 15 carbon atoms, and
        $R_3$ is 2-, 3- or 4-pyridyl, 2- or 3-thienyl, 2- or 3-pyrryl, 2- or 3-furyl, aryl of 6 to 10 carbon atoms, or said aryl substituted by one to three alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms, alkoxycarbonyl of 2 to 8 carbon atoms, hydroxy, nitro, amino, cyano, carboxy, aminocarbonyl, chloro or mixtures of said substituents, and
        (ii) at least stable one nitroxyl compound.

13. A composition according to claim 12 where in the compound of formula I, $R_1$ and $R_2$ are the same.

14. A composition according to claim 13 wherein $R_1$ and $R_2$ are tert-butyl, tert-amyl, tert-octyl, cycloalkyl, α-methylbenzyl or α,α-dimethylbenzyl.

15. A composition according to claim 14 wherein $R_1$ and $R_2$ are tert-butyl, tert-amyl or tert-octyl.

16. A composition according to claim 12 where in the compound of formula I, $R_3$ is phenyl or phenyl substituted by nitro, cyano, dimethylamino, methoxy, alkyl of 1 to 4 carbon atoms, hydroxy or mixtures of said substituents.

17. A composition according to claim 16 where $R_3$ is phenyl.

18. A composition according to claim 12 wherein the monomer of component (a) is an aromatic vinyl compound or an acrylic monomer.

19. A composition according to claim 12 wherein the relative concentrations of component (i) is 5 to 95 percent by weight and of component (ii) is 95 to 5 percent by weight based on the combined total weight of components (i) and (ii) and wherein the effective inhibiting amount of the synergistic mixture of components (i) and (ii) is 1 to 2000 ppm based on the total weight of the monomer of component (a).

20. A process of inhibiting premature polymerization of an ethylenically unsaturated monomer which comprises adding effective inhibiting amount of the synergistic mixture according to claim 12.

21. A process according to claim 20 wherein the monomers are processed at a temperature from 50° C. to 150° C.

22. A process according to claim 20 wherein the synergistic mixture is added continuously or added intermittently upstream to the points where polymerization inhibition is required.

23. A process according to claim 22 wherein the components (i) and (ii) of the synergistic mixture are added separately at different entry points into the process stream in the processing train.

24. A composition according to claim 12 wherein component (i) is
2,6-di-tert-butyl-4-benzylidene-cyclohexa-2,5-dienone,
2,6-di-tert-butyl-4-(4-nitrobenzylidene)-cyclohexa-2,5-dienone,
2,6-di-tert-butyl-4-(3-nitrobenzylidene)-cyclohexa-2,5-dienone,
2,6-di-tert-butyl-4-(4-cyanobenzylidene)-cyclohexa-2,5-dienone,
2,6-di-tert-butyl-4-(4-dimethylaminobenzylidene)-cyclohexa-2,5dienone,
2,6-di-tert-amyl-4-benzylidene-cyclohexa-2,5-dienone,
2,6-di-tert-butyl-4-(4-methoxybenzylidene)-cyclohexa-2,5-dienone, or
2,6-di-tert-butyl-4-(3,5-di-tert-buty-4-hydroxybenzylidene)-cyclohexa-2,5-dienone.

25. A composition according to claim 12 wherein component (ii) is
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl)adipamide,
N-1-oxyl-2,2,6,6-tetramethylpiperidin-4-yl-caprolactam,
N-1-oxyl-2,2,6,6-tetramethylpiperidin-4-yl-dodecylsuccinimide,
2,4,6-tris-[N-butyl-N-(1-oxyl-2,2,6,6-tetramethylpiperidin-4 -yl]-s-triazine,
4,4'-ethylenebis (1-oxyl-2,2,6,6-tetramethylpiperazin-3-one) or
di-tert-butyl nitroxyl.

26. A composition according to claim 12 wherein component (i) is 2,6-di-tert-butyl-4-benzylidene-cyclohexa-2,5-dienone, and component (ii) is bis(1-oxyl-2,2,6,6-tetramethylpiperidin-4-yl) sebacate.

* * * * *

US005616774C1

(12) REEXAMINATION CERTIFICATE (4829th)
United States Patent
Evans et al.

(10) Number: US 5,616,774 C1
(45) Certificate Issued: Aug. 12, 2003

(54) INHIBITION OF UNSATURATED MONOMERS WITH 7-ARYL QUINONE METHIDES

(75) Inventors: Samuel Evans, Marly (CH); Matthew E. Gande, New Fairfield, CT (US); Peter Nesvadba, Yorktown Heights, NY (US); Volker H. von Ahn, Mahopac, NY (US); Roland A. E. Winter, Armonk, NY (US)

(73) Assignee: Ciba-Geigy Corporation, Tarrytown, NY (US)

Reexamination Request:
No. 90/006,280, May 7, 2002

Reexamination Certificate for:
Patent No.: 5,616,774
Issued: Apr. 1, 1997
Appl. No.: 08/422,284
Filed: Apr. 14, 1995

(51) Int. Cl.⁷ ............................................ C07C 69/00
(52) U.S. Cl. ..................... 252/182.18; 585/3; 585/4; 585/5; 252/182.12
(58) Field of Search ................ 585/3, 4, 5; 252/182.18, 252/182.12

(56) References Cited

PUBLICATIONS

N.V. Zolotova et al., "Rate Constants of the Reaction of Methylenequinones with Alkyl Hydrocarbon Radicals", *Kinetics and Catalysis*, vol. 20, No. 1, Part 1, pp. 41–46, Jan.–Feb. 1979 (translated from *Kinetika i Kataliz*, vol. 20, No. 1, pp. 56–61, Jan.–Feb. 1979).

N.V. Zolotova et al., "Reactivity of Methylenequinones as Inhibitors of the Liquid–Phase Oxidation of Hydrocarbons", *Kinetics and Catalysis*, vol. 20, No. 1, Part 1, pp. 34–40, Jan.–Feb. 1979 (translated from *Kinetika i Kataliz*, vol. 20, No. 1, pp. 48–55, Jan.–Feb. 1979 by Plenum Publishing Corp.).

A.A. Volod'kin et al., "Stable Methylenequinones", *Russian Chemical Reviews*, 57 (4), pp. 336–348, 1988 (translated from *Uspekhi Khimii*, 57, pp. 595–624, 1988).

*Primary Examiner*—Jean F. Vollano

(57) ABSTRACT

Ethylenically unsaturated monomers are protected from premature polymerization during manufacture and storage by the incorporation therein of an effective stabilizing amount of a 7-aryl quinone methide compound.

US 5,616,774 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 12–26 is confirmed.

Claims 1–11 are cancelled.

New claims 27–29 are added and determined to be patentable.

*27. A composition for inhibiting the premature polymerization of an ethylenically unsaturated monomer which comprises*

*(a) an ethylenically unsaturated monomer or mixture of monomers, and*

*(b) from 1 to 2,000 ppm, based on the weight of the monomer of component (a) of a compound I selected from the group consisting of*
    *2,6-di-tert-butyl-4-(4-nitrobenzylidene)-cyclohexa-2,5-dienone,*
    *2,6-di-tert-butyl-4-(3-nitrobenzylidene)-cyclohexa-2,5-dienone,*
    *2,6-di-tert-butyl-4-(4-cyanobenzylidene)-cyclohexa-2,5-dienone,*
    *2,6-di-tert-butyl-4-(4-dimethylaminobenzylidene)-cyclohexa-2,5-dienone,*
    *2,6-di-tert-amyl-4-benzylidene-cyclohexa-2,5-dienone,*
    *2,6-di-tert-butyl-4-(4-methoxybenzylidene)-cyclohexa-2,5-dienone and*
    *2,6-di-tert-butyl-4-(3,5-di-tert-butyl-4-hydroxybenzylidene)-cyclohexa-2,5-dienone.*

*28. A composition according to claim 27 wherein the monomer of component (a) is an aromatic vinyl compound or an acrylic monomer.*

*29. A process for inhibiting the premature polymerization of an ethylenically unsaturated monomer which comprises adding thereto from 1 to 2,000 ppm, based on the weight of the monomer of component (a), of the compound I according to claim 27.*

\* \* \* \* \*